US008626528B2

(12) United States Patent
Bisera et al.

(10) Patent No.: US 8,626,528 B2
(45) Date of Patent: Jan. 7, 2014

(54) INTELLIGENT ALARMS

(75) Inventors: Joe Bisera, Camarillo, CA (US); Wanchun Tang, Palm Desert, CA (US)

(73) Assignee: Weil Institute of Critical Care Medicine, Rancho Mirage, CA (US)

( * ) Notice: Subject to any disclaimer, the term of this patent is extended or adjusted under 35 U.S.C. 154(b) by 168 days.

(21) Appl. No.: 13/212,124

(22) Filed: Aug. 17, 2011

(65) Prior Publication Data
US 2013/0046158 A1 Feb. 21, 2013

(51) Int. Cl.
*G06Q 50/00* (2012.01)
(52) U.S. Cl.
USPC .............................................. 705/2
(58) Field of Classification Search
USPC ............................. 705/2, 3; 600/301
See application file for complete search history.

(56) References Cited

U.S. PATENT DOCUMENTS

2002/0169636 A1* 11/2002 Eggers et al. ............... 705/3
2010/0069725 A1* 3/2010 Al-Ali ...................... 600/301

OTHER PUBLICATIONS

Merriam-Webster on-line dictionary: definintion for the word "critical".*

* cited by examiner

*Primary Examiner* — John Pauls
(74) *Attorney, Agent, or Firm* — Lawrence S. Cohen

(57) ABSTRACT

A patient in intensive care is monitored by connecting the outputs of a plurality of sensors to a computer, where the sensors all relate to one mode of functioning such as heart beating, respiration, infusion of a liquid into the patient, etc. The sensor outputs are delivered to a computer that sounds an alarm, only if all sensors that indicate one function (e.g. heart beating) indicate dangerously low operation of that function. This avoids many false alarms caused by one sensor having a low output such as due to accidental disconnection of a wire.

7 Claims, 1 Drawing Sheet

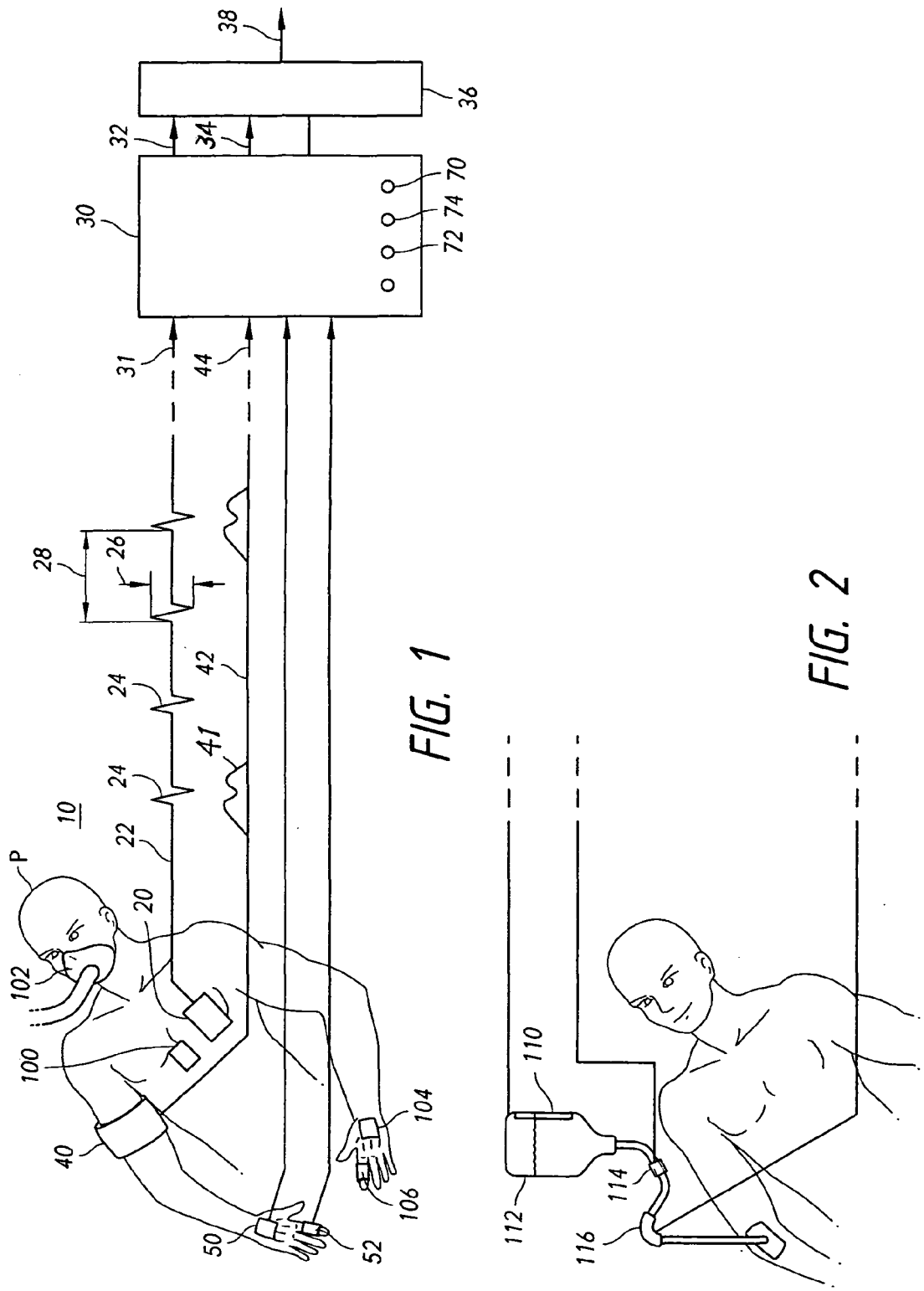

INTELLIGENT ALARMS

BACKGROUND OF THE INVENTION

False sound alarms are one of the greatest annoyances in critical care settings, such as an ICU (intensive care unit) environment. In fact, more than 97% of sound alarms are false positive alarms. Sometimes caregivers disable the alarms, which can result in preventable fatal events. A system that minimized false alarms while sounding legitimate alarms, would be of value.

SUMMARY OF THE INVENTION

The present invention provides apparatus and methods for reducing and prioritizing alarms based on sensors that sense cardiovascular patterns, respiratory patterns, electrocardiogram patterns, pulse rate and pulse strength, oxygen saturation such as is sensed by a pulse oximeter, and arterial pressure. Sensors can include those that sense central venous pressure, pulse morphology as well as arterial pressure wave forms, end tital $PCO_2$ (partial pressure of $CO_2$), operation of a ventilator, and operation of an infusion pump. By providing a plurality of sensors that each indicates one function, the failure of one sensor can be overridden by the outputs of other sensor(s).

The novel features of the invention are set forth with particularity in the appended claims. The invention will be best understood from the following description when read in conjunction with the accompanying drawings.

BRIEF DESCRIPTION OF THE DRAWINGS

FIG. 1 is view of a patient in an ICU environment, with sensors that sense functioning related to beating of a patient's heart.

FIG. 2 is a view similar to that of FIG. 1, with sensors related to infusion.

DETAILED DESCRIPTION OF THE INVENTION

FIG. 1 shows a patient P in an intensive care environment 10, wherein the patient is coupled to several sensors that monitor the functioning of various systems of the patient's body. These sensors include heart function sensors comprising a patient heart sensor 20 whose output 22 includes electrical pulses 24 of measurable height 26 and measurable spacing 28. The output of the sensor is delivered to a first input 31 of a computer 30 which measures the height and spacing of the heart pulses. If the pulse height 26 is below a selected height or the spacing 28 has increased to more than a predetermined spacing then the computer generates a failure signal on an output 32. Another sensor 40 senses the blood pressure, indicated at 41, of the patient. A signal representing the blood pressure is delivered to computer input 44. If the signal 41 indicates failure (e.g. the difference, between systolic and diastolic pressure is less than a certain minimum), a blood pressure signal output 34 is delivered. The outputs 32, 34 delivered to part 36 of the computer results in sound alarm signal 38 only if all outputs 32, 42 indicate failure of patient heart functioning.

Another sensor 50 senses the oxygen saturation of the patient's blood and delivers a signal to computer input 51. Still another sensor 52 senses the $PCO_2$ (partial pressure of carbon dioxide) in the patient's blood and delivers a corresponding signal to computer input 53. A pulse oximeter can be used to sense $PCO_2$. If the output 51 of the sensor 50 shows at least a limited level of oxygen in the patient's blood, then this means that the heart is beating to circulate the blood through the lungs to pick up oxygen. If the output 53 of sensor 52 shows at least a predetermined minimum of carbon dioxide then this indicates that the patient's blood is circulating. The computer will not generate an emergency sound alarm so long as one of the sensors 20, 40, 50, 52 indicates that the patient's heart is beating regularly, or at least does not indicate failure.

If the patient's heart is not beating regularly, then this is a critical failure that should be rectified immediately. The term "critical" means life threatening, or danger of death. If the output 22 of sensor 20 shows a pulse spacing 28 greater than a predetermined limit such as less than one pulse per three seconds, or shows a pulse height 26 less than one-fourth of the average previous height when a nurse determined that the heart was beating appropriately, then this indicates a critical failure that should be rectified immediately. However, if the output of the blood pressure sensor 40 or the output of sensor 50 or 52 is more than a minimal level, then this indicates that the heart is beating properly, or at least is beating sufficiently that this is not a critical situation. Actually, an improper output of only one sensor such as sensor 20, indicates that one of the wires that connects to the heart rate sensor 20 has been disconnected or is not connected in a low resistance connection. Functioning of the other sensors 50, 52 indicate that the heart is beating. When the computer senses a bad output, or failure from one sensor but other sensors indicate otherwise, then the computer 30 generates a visual indication such as at 70 that the heart rate sensor 20 or the blood pressure sensor 40 or other sensors such as 50 or 52 indicate improper heart functioning then lights at 72, 74 light up. It is easier for a nurse to check these sensors which cause a light 70, 72 etc. to light up when he/she has time, than to treat a poor sensor output as an emergency that requires he/she to drop everything to concentrate on the emergency.

Another function that is commonly monitored in an ICU is patient respiration. Sensors that indicate breathing include a chest vertical expansion-contraction sensor 100, an air flow sensor 102, an oxygen saturation sensor 104 and a $PCO_2$ sensor 106. If any of these respiration sensors indicate respiration, then no alarm will be sounded, although a visual indication will be generated that the sensor is not functioning properly.

Another function that is commonly monitored in an ICU is proper operation of an infusion pump that infuses one to several different fluids, including a saline solution, an anti-microbial fluid, etc. For those infusions that are critical, applicant can provide sensors including a sensor 110 (FIG. 2) that detects the level of fluid in a container 112 from which the fluid in introduced into the patient. The computer 30 sounds an alarm if the level does not decrease as expected, from the initial level existing when a nurse first connected the fluid container to the infusion pump, and other sensor(s) also indicate improper infusion. Sensor 114 senses movement of liquid in an infusion tube. Sensor 116 senses the pressure of air in the infusion tube.

The visual indicators preferably indicate different levels of importance. In one example, a particular one of a plurality of sensors does not agree with the other sensors for a critical function such as heart rate, breathing, infusion, and that sensor seldom malfunctions. Then, the visual indicator 70 may be a light that flashes on and off. Other visual indicators may include the continuous display of a color such as from a steady light.

Thus, the invention provides a system for generating alarms, where the system includes a plurality of sensors that sense functioning that indicates the same general condition such as heart beating, respiration, or infusion. The system generates a sound alarm indicating that a caregiver's attention is required immediately, only if all sensors indicate a patient malfunction for the particular condition. If one or more sensors indicate proper functioning, or at least temporarily acceptable functioning, then a visual indicator is operated, but a sound alarm is not sounded.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. Apparatus for use in an intensive care unit of a medical care facility for monitoring a patient, comprising:
    a plurality of groups of sensors, each group of the plurality of groups of sensors including at least three sensors connected to the patient, wherein each of the at least three sensors of a particular group of sensors monitors a different corresponding physiological condition of the same organ of the patient that can fail is such a way that it threatens the life of the patient;
    said apparatus further comprising:
    a computer that has a plurality of inputs, each input is connected to a different one of the at least three sensors for each of the plurality of groups of sensors; and
    wherein, each of the at least three sensors for each of the plurality of groups of sensors has an output that is representative of the corresponding physiological condition, and wherein the computer generates a sensor failure output for a particular sensor when the corresponding physiological condition of the patient is outside of a selected range, above or below a selected limit, or when a particular sensors is no longer connected to either the patient, the computer, or both; and
    wherein, said computer is configured to operate a visual alarm when one or more of, but not all of, said sensors in one or more of the plurality of groups of sensors has a corresponding sensor failure output generated; and
    wherein, said computer is further configured to operate a sound alarm only when all of the at least three sensors for at least one of the plurality of groups of sensors has a corresponding sensor failure output generated.

2. The apparatus described in claim 1 wherein:
    said plurality of groups of sensors includes at least a first group of sensors that includes at least three heart function sensors; a second group of sensors that includes at least three breathing function sensors and a third group of sensors that include at least three infusion sensors.

3. The apparatus described in claim 2 wherein:
    said first group of sensors that includes at least three heart function sensors comprising:
    a first heart function sensor wherein the sensor failure output is generated when the patient heart rate is below a first selected limit;
    a second heart function sensor wherein the sensor failure output is generated when the patient oxygen saturation is below a second selected limit;
    a third heart function sensor wherein the sensor failure output is generated when the patient blood pressure is below a third selected limit.

4. The apparatus described in claim 2 wherein:
    said second group of sensors that includes at least three breathing function sensors comprising:
    a first breathing function wherein the sensor failure output is generated when the patient heart beats below a predetermined magnitude or at a rate below a fourth selected limit, using an electrocardiogram;
    a second breathing function sensor wherein the sensor failure output is generated when the patient blood pressure is below a fifth selected limit;
    a third breathing function sensor wherein the sensor failure output is generated when the patient partial pressure of $CO_2$ is below a sixth selected limit.

5. The apparatus described in claim 2 wherein:
    said third group of sensors that includes at least three infusion sensors comprising:
    a first infusion sensor that detects the flow rate of a liquid through a tube that leads into the patient and wherein the sensor failure output is generated when the flow rate is below a seventh selected limit;
    a second infusion sensor that detects the height of said liquid in a bottle that connects to the patient and wherein the sensor failure output is generated when the height is below an eighth selected limit; and
    a third infusion sensor that detects the back pressure at the infusion site and wherein the sensor failure output is generated when the back pressure is above a ninth selected limit.

6. The apparatus described in claim 1 wherein:
    said computer has a recording circuit that records variations in the output of each of the at least three sensors in each of the plurality of groups of sensors over a predetermined time period; and
    operates the sound alarm output only when the magnitude of variations for all of the at least three sensors for at least one of the plurality of groups of sensors exceeds a predetermined variation in said time period.

7. A method for use in an intensive care unit of a medical care facility for monitoring a patient, the method comprising:
    providing a plurality of groups of sensors configured to be connected to the patient, wherein each group of the plurality of groups of sensors includes at least three sensors, and wherein each of the at least three sensors of a particular group monitors a different corresponding physiological condition of the same organ of the patient that can fail in a way that threatens the life of the patient;
    wherein, each of the at least three sensors for each of the plurality of groups of sensors has an output that is representative of the corresponding physiological condition;
    connecting the outputs of each of the at least three sensors of each of said plurality of said groups of sensors, to a different one of a plurality of inputs of a computer;
    detecting, via the computer, that the corresponding physiological condition of the patient is outside of a selected range, above or below a selected limit, or that a particular sensor is no longer connected either to the patient or to the computer, or both and in response to the detecting, generating, via the computer, a sensor failure output;
    analyzing the sensor outputs, via the computer, wherein the computer is configured to operate a visual alarm when one or more of, but not all of, said sensors in one or more of the plurality of groups of sensors has a corresponding sensor failure output generated, and to operate a sound alarm only when all of the at least three sensors for at least one of the plurality of groups of sensors has a corresponding sensor failure output generated.

* * * * *